United States Patent [19]

Pierce, Jr.

[11] Patent Number: 5,059,613
[45] Date of Patent: Oct. 22, 1991

[54] TOPICALLY ACTIVE OCULAR BENZOTHIAZOLE SULFONAMIDE CARBONIC ANHYDRASE INHIBITORS

[75] Inventor: William M. Pierce, Jr., Louisville, Ky.

[73] Assignee: Research Corporation Technologies, Inc., Tucson, Ariz.

[21] Appl. No.: 495,551

[22] Filed: Mar. 19, 1990

[51] Int. Cl.$^5$ .................. C07D 277/80; A61K 31/125
[52] U.S. Cl. ...................................... 514/367; 548/166
[58] Field of Search ........................ 548/166; 514/367

[56] References Cited

U.S. PATENT DOCUMENTS

| | | |
|---|---|---|
| 3,323,999 | 6/1967 | Nechay et al. ........................ 514/367 |
| 4,386,098 | 5/1983 | Woltersdorf, Jr. et al. ......... 514/367 |
| 4,416,890 | 11/1983 | Woltersdorf, Jr. .................. 514/367 |
| 4,424,227 | 1/1984 | Robert ................................. 514/367 |
| 4,426,388 | 1/1984 | Woltersdorf, Jr. .................. 514/367 |
| 4,454,148 | 6/1984 | Woltersdorf, Jr. et al. ......... 514/367 |
| 4,456,599 | 6/1984 | Woltersdorf, Jr. .................. 514/367 |
| 4,470,991 | 9/1984 | Woltersdorf, Jr. .................. 514/367 |
| 4,472,417 | 9/1984 | Woltersdorf, Jr. .................. 514/367 |
| 4,472,418 | 9/1984 | Woltersdorf, Jr. .................. 514/367 |
| 4,483,864 | 11/1984 | Barfknecht et al. ................. 514/367 |
| 4,483,872 | 11/1984 | Barfknecht et al. ................. 514/367 |
| 4,500,538 | 2/1985 | Woltersdorf ........................ 514/367 |
| 4,505,923 | 3/1985 | Hoffman ............................. 514/224 |
| 4,510,155 | 4/1985 | Smith et al. ........................ 514/367 |
| 4,619,939 | 10/1986 | Maren .................................. 514/367 |
| 4,629,738 | 12/1986 | Barfknecht et al. ................. 514/367 |
| 4,636,515 | 1/1987 | Barfknecht et al. ................. 514/367 |

OTHER PUBLICATIONS

Schoenwald et al., *J. Med. Chem.*, 1984, 27: 810–812.
Ponticello et al., *J. Med. Chem.*, 1987, 30: 591–597.
Maren et al., *The Journal of Pharmacology and Experimental Therapeutics*, 1987, 241: 56–63.
Maren, *Drug Development Research*, 1987, 10: 255–276.
Maren et al., *Exp. Eye Res.*, 1983, 36: 457–480.
Maren et al., *Current Eye Research*, 1985, 4: 399–408.
Pierce, Jr. et al., *Research Communications in Chemical Pathology and Pharmacology*, 1985, 50: 3–20.
Eller et al., *Journal of Pharmaceutical Sciences*, 1985, 74:5; 525–529.

Primary Examiner—Robert Gerstl
Attorney, Agent, or Firm—Scully, Scott, Murphy & Presser

[57] ABSTRACT

This invention is directed to compounds of the formula

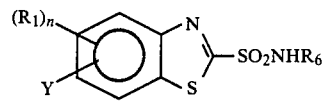

and pharmaceutically acceptable salts thereof wherein
R$_6$ is hydrogen or lower alkyl;
each R$_1$ is hydrogen, lower alkyl, halogen, nitro, trihaloalkyl, lower alkoxy, formyl, lower alkanoyl, loweralkylamino or diloweralkylamino

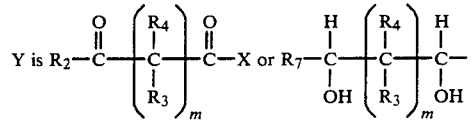

X is O, S or NR$_5$;
R$_2$ is OR$_7$ or NR$_7$R$_8$;
each R$_3$ and R$_4$ are independently hydrogen or lower alkyl;
R$_5$ R$_7$ and R$_8$ are independently hydrogen or lower alkyl;
n is 0–3 and
m is 0–6.

These compounds are useful for treating glaucoma or assessing corneal function in mammals.

32 Claims, No Drawings

TOPICALLY ACTIVE OCULAR BENZOTHIAZOLE SULFONAMIDE CARBONIC ANHYDRASE INHIBITORS

BACKGROUND OF THE INVENTION

This invention relates to derivatives of benzothiazoles useful as carbonic anhydrase inhibitors (CAI) and pharmaceutically effective salts thereof. More particularly, the compounds of the invention are useful in the treatment of glaucoma and assessment of corneal function.

FIELD OF THE INVENTION

Carbonic anhydrase is an enzyme which secretes acidic or basic fluids in a variety of tissues, including the eye, pancreas, choroid plexus of the central nervous system, kidney, bone and stomach. Carbonic anhydrase mediated secretion is a target for pharmacotherapy and a host of pathologies. The compounds of the present invention are useful in the treatment of and prophylaxis of these pathologies, such as peptic ulcers disease (by inhibiting gastric acid secretion), altitude sickness, epilepsy, or as a diuretic.

Another pathological state characterized by in appropriate carbonic anhydrase secretion is metabolic bone disease, such as osteoporosis. The compounds of the present invention inhibit bone resorption and are thus useful for the treatment and prophylaxis of metabolic bone disorders.

Glaucoma is another pathological state caused by inappropriate carbonic anhydrase mediated secretion. The compounds of the present invention are useful in the management of glaucoma and assessment of corneal function.

The term glaucoma refers to a group of eye diseases often characterized by elevated intraocular pressure (IOP). Accompanying this increased IOP is a restriction of blood supply to the optic nerve and, if uncontrolled, loss of vision. Much of the pharmacotherapeutic management of glaucoma is accomplished by use of agents which are autonomic nervous system agonists or antagonists. The goal of such therapies is reduction in inflow of aqueous humor or improvement of outflow facility.

A class of drugs, the carbonic anhydrase inhibitors (CAI), have been used to diminish aqueous humor inflow by inhibition of carbonic anhydrase (CA). The prototypical acetazolamide (AT) was shown to decrease IOP following oral administration. B. Becker, *Am. J. Opthalmol.*, 38, 16–17 (1954). Findings such as these with other CAI led to a flurry of hopeful research and clinical activity in the preparation of these drugs. The CAI are in general rather non-toxic, and oral administration of CAI does diminish IOP; however, the incidence and severity of side effects have limited patient compliance and hence clinical efficacy. These side effects include depression, fatigue, anorexia and paresthesia. Due to the incidence of these side effects, upon systemic administration of inhibitors, topical administration has been attempted. Under these conditions, however, the most potent CAI (as described in vitro) do not lower IOP.

Recently, efforts have been renewed in the quest for a topical CAI for the lowering of IOP. Several syntheses have yielded inhibitors which are effective in lowering IOP. See, T. H. Maren, et al. *Exp. Eye. Res.*, 36, 457–480 (1983). One such agent, aminozolamide, has been tested, and found to be partially effective in clinical trial. See, R. A. Lewis, et al. *Arch. Ophthalmol.*, 104, 842–844 (1986). Other studies have modified methazolamide and ethoxzolamide, which are classical CAI, and have formed compounds having increased corneal permeability. Another approach is the synthesis of prodrugs, e.g., an ester of the hydroxy analogue of ethoxzolamide, which is subject to hydrolysis by esterases as it traverses the cornea, yielding an active inhibitor. See, J. Pharmacol. *Exp. Ther.* 232, 534–540 (1985).

Other groups are developing a new class of CAI which as also effective as an ocular hypotensive agent. See, R. F. Ward, et al., *Abstracts of the Annual Meeting of the American Society for Research in Vision and Ophthalmology*, p16, #7 (1988).

These studies have focused on topical delivery of novel CA inhibitors to diminish systemic side effects. The cornea is a barrier of mixed hydrophobic and hydrophillic properties, due to both cell and stromal layers. Successful penetration of the cornea requires either 1) a drug which of itself has substantial aqueous and lipid solubilities or 2) a prodrug which is lipophilic but is hydrolyzed by cornea epithilial esterases to yield a more hydrophilic active drug.

The endothelium of the cornea is a cell layer on the posterior aspect of the cornea which functions to maintain a dehydrated, transparent cornea. Carbonic anhydrase plays a role in this dehydration function, and inhibition of cornea endothelial carbonic anhydrase leads to corneal swelling. Administration of CAI topically to the cornea, followed by measurement of corneal thickness, yields a measure of corneal endothelial functional integrity. From this measurement, the corneal surgeon can differentiate between sufficient and defective corneas and can make a determination whether donor cornea transplant is necessary.

SUMMARY OF THE INVENTION

This invention is directed to novel compounds useful in the treatment of glaucoma having the general formula

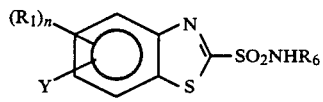

and pharmaceutically acceptable salts thereof wherein $R_6$ is hydrogen or lower alkyl;

each $R_1$ is hydrogen, lower alkyl, halogen, nitro, trihaloalkyl, lower alkoxy, formyl, lower alkanoyl loweralkylamino or diloweralkylamino;

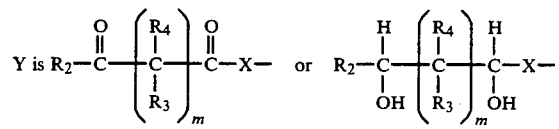

X is O or $NR_5$ or S;

$R_2$ is $OR_7$ or $NR_7R_8$;

each $R_3$ and $R_4$ are hydrogen or lower alkyl;

$R_5$, $R_7$ and $R_8$ are independently hydrogen or lower alkyl;

m is 0–6, and n is 0–3.

DETAILED DESCRIPTION OF THE INVENTION

The lower alkyl groups, when used singly or in combination with other groups, contain from one to six carbon atoms and may be straight chain or branched. This group includes such groups as methyl, ethyl, propyl, isopropyl, butyl, t-butyl, sec-butyl, isobutyl, amyl, hexyl and the like. In a preferred form the lower alkyl contains from one to four carbon atoms. The most preferred alkyl group is methyl.

As defined herein, halo when used singly or in combination with other groups refers to chloro, bromo, iodo or fluoro. The most preferred halo group is fluoro.

The alkanoyl groups, as defined herein, contain from two to six carbon atoms, containing one carbonyl group. In a preferred embodiment, alkanoyl is acetyl or pivaloyl or butyryl.

In a preferred embodiment, $R_6$ is hydrogen thereby defining the $SO_2NH_2$ moiety.

In the formula hereinabove, when n is 0, then the benzo group of the benzothiazole is unsubstituted except for Y. Furthermore, when $R_1$ is hydrogen and n is 0–3, then the benzo group of the benzothiazole is unsubstituted except for Y. However, when $R_1$ is other than hydrogen and n is 1, then the benzo group is disubstituted, it contains Y and $R_1$. In the case when n is 2 and each $R_1$ is other than hydrogen, then the benzo ring is trisubstituted, it contains two $R_1$'s and Y. Finally, when n is 3 and each $R_1$ is other than hydrogen, then the benzo ring is tetrasubstituted, 3 $R_1$'s and one Y.

In the cases when n is 2 or 3, however, each $R_1$ substitutent may be the same or different in accordance with the definitions hereinabove.

The preferred $R_1$ group is hydrogen or lower alkyl. The most preferred $R_1$ group is hydrogen.

As defined herein, Y is

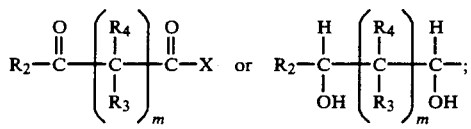

It is preferred that $R_2$ is $OR_7$ or $NR_7R_8$, and that $R_7$ is an alkyl group containing 2–4 carbon atoms and $R_8$ is hydrogen or alkyl containing 2–4 carbon atoms.

The term

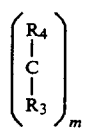

refers to the group

being repeated m times. For example, when m is 2, the group

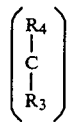

becomes

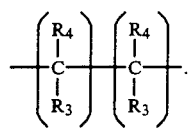

However, each $R_3$ and each $R_4$ within the group or between the group

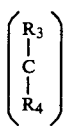

may be the same or different. Thus, for example, when

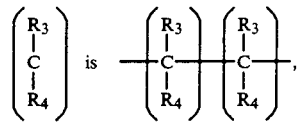

one $R_3$ may be hydrogen, while the other $R_3$ may be alkyl. The same is also true for $R_4$. The preferred definitions of $R_3$ and $R_4$ are independently hydrogen or methyl. It is especially preferred that at least one of $R_3$ and $R_4$ is hydrogen. It is most preferred that both $R_3$ and $R_4$ are hydrogen.

The preferred values of m are 0, 2, 4 or 6 with the most preferred being 0, 2 or 4.

The "X" group acts as the bridge linking the benzo portion of the molecule to the acyl group. It is preferred that X is O or $NR_5$ wherein $R_5$ is hydrogen or lower alkyl. It is especially preferred that X is O or NH. The most preferred value of X is NH.

A preferred embodiment of the present application has the formula

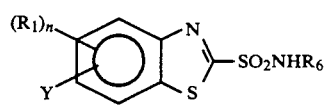

wherein Y is defined as

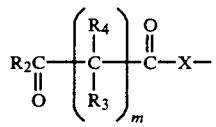

and X, $R_1$, $R_6$, $R_2$, $R_3$, $R_4$, $R_7$, $R_8$, and m and n being as defined hereinabove.

An especially preferred embodiment has the formula

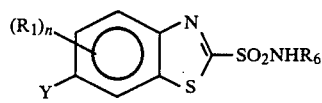

The compounds of the present invention wherein

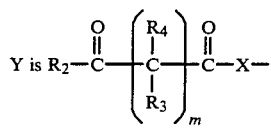

can be prepared by art recognized techniques. For example, the benzothiazole of Formula II can be reacted with an acylating derivative of Formula III under amide or ester forming conditions to form a compound of Formula I as follows:

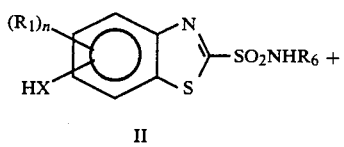

II

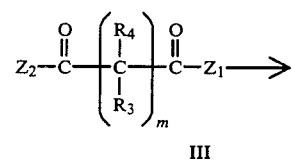

III

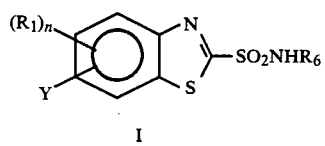

I

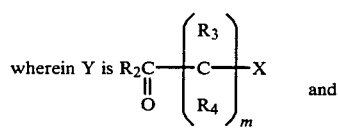

and wherein $Z_1$ is OH or halogen and $Z_2$ is $R_2$ or a protected $R_2$ and X is O or $NR_5$; $R_1$, $R_3$, $R_4$, $R_5$, $R_6$, $R_7$, $R_8$, n and m are as defined hereinabove. It is preferred that $Z_1$ is halogen with the most preferred halogen being chlorine. If $R_2$ in the final product is $OR_7$ and $R_7$ is hydrogen, then $R_2$ should be protected in order to minimize side reactions from occurring. Protecting groups of this sort are well known in the art. Examples of many of those possible groups may be found in "Protective Groups in Organic Synthesis" by T. W. Green, John Wiley and Sons, 1981 which is incorporated herein by reference. For example, $Z_2$ may be benzyloxymethyl ester which may be removed by mild condition, i.e., catalytic hydrogenation to form the corresponding acid.

This reaction can be effected in any inert solvent in which the reactants are soluble. These solvents include diethyl ether, tetrahydrofuran, dioxane, benzene, toluene and the like. This reaction is run at effective temperatures, usually at about room temperature or slightly elevated temperatures. However, the reaction may be carried out at temperatures ranging from 0° to the boiling point of the reaction mixtures.

The compounds of Formula II can be prepared by art recognized techniques. The following is exemplary:

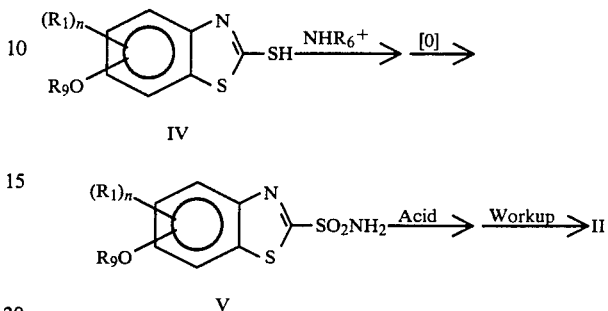

In these reactions $R_9$ is lower alkyl and $R_1$, $R_2$, $R_3$, $R_4$, $R_5$, $R_6$, $R_7$, n and m, are as defined hereinabove. In the above sequence, the thiol of Formula IV is reacted with an alkylamine salt solution under oxidizing conditions such as ammonium hydroxide, and sodium hypochlorite in aqueous solutions, followed by oxidation with an oxidizing agent, such as potassium permanganate, to form the sulfonamide of Formula V. These reactions should be conducted at low temperatures ranging from about −25° C. to 25° C., although it is preferred that the reaction is run at approximately 0° C. Furthermore, the oxidation step should be conducted in a solvent in which the reagents are soluble, such as acetone.

The $R_9$ group is then removed by art recognized techniques. For example, reaction of V with a Lewis acid, such as $BF_3$, $BBr_3$ or $AlCl_3$ in an inert solvent, such as chloroform, methylene chloride and the like at low temperatures, ranging from −0° C. to −100° C. and preferably at −80° C., cleaves the ether group and work-up in water provides the product II, wherein $R_9$ is hydrogen.

The hydroxy group on the benzo moiety can be replaced by an $NH_2$ group by art recognized techniques. An exemplary procedure is described hereinbelow:

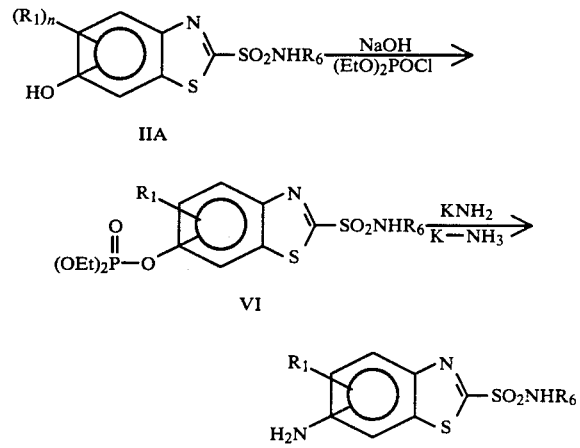

IIA is first converted to diethyl phosphate derivative which is then treated with $KNH_2$ and potassium metal in liquid ammonia in accordance with the procedure described by Rossi, et al., in *J. Org. Chem.*, 37, 3570 (1972) which is incorporated herein by reference. The primary amine can be converted to a secondary amine by reacting an excess IIB with an alkyl halide, $R_5E$, wherein E is halo, preferably bromo or chloro under amine-alkylating conditions.

The reduced derivatives of the biscarbonyl compounds are formed from the corresponding dicarbonyl compounds of Formula I i.e., compounds of Formula I wherein Y

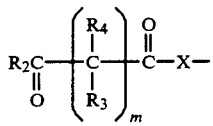

by art recognized techniques known to one skilled in the art. More specifically, reducing agents, such as $LiAlH_4$, and the like, can be used to effect the reduction of the two carbonyl groups and form the corresponding diol.

The compounds of the invention containing basic nitrogen form salts with acids, both organic and inorganic acids. Of particular value are salts with pharmaceutically-acceptable acids especially in dosage forms predicated on aqueous systems where the enhanced water solubility of the salts is most advantageous. Salts formed with pharmaceutically unacceptable acids are also useful in the isolation and purification of the basic nitrogen-containing new compounds. Salts include those formed with hydrochloric, sulfuric, nitric, perchloric, benzenesulfonic, toluenesulfonic, phosphoric, acetic, malic, malonic, tartaric and similar such acids.

The compounds of the invention also exist in stereoisomeric forms due to the presence of asymmetric centers in the molecule. This invention contemplates the various stereoisomers, i.e., enantomers or diastereomers, individually or in mixtures such as the racemic mixture. The individual stereoisomers can be obtained by standard resolution procedures known to those skilled in the art or by stereospecific synthesis.

The compounds or compositions of the present invention can be administered to the host in a variety of forms adapted to the chosen route of administration, i.e., orally, topically, intravenously, intramuscularly or subcutaneous routes. The preferred route of administration for ocular use is topical administration to the cornea.

In using the compounds or compositions of this invention for treatment of glaucoma topically, the compound may be carried in an inert, non-eye irritating, non-toxic eye drop diluent of conventional formulation. Such formulations are well known, and commonly referred to in, for example, the Physician's Desk Reference for Ophthalmology (1982 Edition, published by Medical Economics Company, Inc., Oridell, N.J.), wherein numerous sterile ophthalmologic ocular solutions are reported, e.g., see pp. 112-114, which are incorporated herein by reference.

Preferably the amount of the carbonic anhydrase inhibitors present in the eye drop treatment composition is concentration of from about 0.25% to about 5% by weight of the eye drop treating composition. Most preferably, the amount is from about 0.5% to about 2.0% by weight of the eye drop treating composition, and in tests conducted to date highly effective compositions have used the compounds at the 1% suspension level.

As heretofore mentioned, it is preferred that the diluent be an isotonic eye treatment carrier, buffered to a pH within the range of from about 4.0 to about 8.0 and containing a small but effective amount of a wetting agent and an anti-bacterial agent. The preferred pH range is from about 5.0 to about 7.8.

Commonly used wetting agents are well known, and again are mentioned in the previously referred to pages of the *Physician's Desk Reference for Ophthalmology*. One suitable one is Tween, and in particular, Tween 80. Likewise, anti-bacterials are known and commonly employed in such compositions. Suitable anti-bacterials include the most preferred benzalkonium chloride. Other anti-bacterials can also be used, such as, for example, chlorobutanol. The amount of wetting agent can range from 0.01% to 0.10%. The amount of anti-bacterial can range from about 0.004% to about 0.02% by weight of the eye drop treating composition.

The compounds of the invention may also be delivered by more sustained delivery devices implanted or apposed directly to the cornea. The active compound may be associated with a shield, wafer or insert. By association, it is meant that the compound may be chemically bonded to or physically incorporated with the shield, wafer or insert.

The compounds of this invention, are not only water soluble, but they also have a lipid solubility factor to allow transfer across the eye, and they have suitable structure to allow them to effectively function in the eye as carbonic anhydrase inhibitors per se, or following metabolic activation. Their water solubility means ease of preparation for topical application, their lipid solubility characteristics mean effectiveness in transfer across the cornea and into the target site (ciliary body).

In the treatment and prophylaxis of the other pathologies discussed hereinabove, such as osteoporosis as well as in the prophylaxis and treatment of glaucoma, the active compound may also be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently contain an amount of active compound in such therapeutically useful compositions is such that a suitable dosage will be obtained. Preferred compositions or preparations according to the present invention are prepared so that an oral dosage unit form contains between about 50 and 500 mg of active compound. In a more preferred form, an oral dosage unit will contain from about 50 mg to about 100 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl propylparabens as preservatives, a dye and flavoring such as cherry or orange flavor. Of course, any material used preparing any dosage unit form should be pharmaceutically pure and substantially non-toxic in the amounts employed. In addition, the active compound may be incorporated sustained-release preparations and formulations.

The active compound may also be administered parenterally. Solutions of the active compound or pharmacologically acceptable salt can be prepared in water suitably mixed with a viscosity agent e.g. hydroxyalkyl cellulose, such as hydroxypropylmethylcellulose or hydroxyethylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersions medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include agents, which yield isotonic solutions, for example, sugars or sodium chloride. Prolonged absorption of which yield isotonic solutions, the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solution, the preferred methods of preparation are vacuum drying and the freeze-drying technique which yield a powder of the active ingredient plus any additional desired ingredient from previously sterile-filtered solution thereof.

The invention is further illustrated by the following examples.

EXAMPLE 1

6-Hydroxy-2-benzothiazole Sulfonamide

A. 6-Ethoxy-2-benzothiazolesulfonamide.

A solution of ammonium hydroxide (650 mL) was cooled to 0° C. in an ice/methanol bath. A solution containing 6-ethoxy-2-mercapto-benzothiazole (16.0 g, 0.076 mol) in 170 mL of 5% NaOH and a solution of 5.25% NaOCl (150 mL) were added simultaneously to the ammonium hydroxide solution while maintaining a temperature of 0° C. The reaction was stirred for 15 min. upon completing the addition, and the sulfenamide was collected by vacuum filtration. The sulfenamide was dissolved in 1 L of acetone and oxidized by the addition of 450 mL of 5% KMnO4 over 4 hours. The MnO2 was removed by filtering through Celite, and the acetone was removed under vacuum. The product was precipitated from solution by acidification with concentrated HCl to yield 11.7 g (59.7%) of 6-ethoxy-2-benzothiazolesulfonamide, which was purified by dissolving it in 5% NaOH, filtering, and precipitating with concentrated HCl; mp 190°-191° C.; MS, m/e 258 (M,calcd 258).

B. 6-Hydroxy-2-benzothiazolesulfonamide

A 1 M solution of BBr3 in CH2Cl2 (23 mL, 0.022 mol) was cooled to −80° C. in a dry ice/acetone bath under a N2 atmosphere. A suspension of 6-ethoxy-2-benzothiazolesulfonamide (0.5 g, 0.002 mol) in 75 mL of CH2Cl2 was added slowly to the cooled BBR3 solution The reaction was removed from the cooling bath and stirred at room temperature for 15 hours. It was poured into ice-water, stirred for 30 min, and filtered to Yield 0.35 g of product (73.8%). The product was purified by recrystallization from MeOH/H2O; mp 209°-212° C.; M/S m/e 230 (M,calcd 230).

EXAMPLE 2

6-(Ethyloxalyloxy)-2-benzothiazole sulfonamide

6-Hydroxybenzothiazolesulfonamide (0.09 mol), prepared in accordance with the procedure described in Example 1 is added to a solution of 400 ml dry THF and, 0.11 mol. pyridine. Ethyloxaloyl chloride (0.09 mol) in 100 2 ml of diethyl ether is added slowly with stirring. After the reaction is completed, it is quenched by adding 35 mL water. The water is separated off and the organic solvents are removed under reduced pressure to form the above-identified product.

EXAMPLE 3

6-(Ethylsuccinyloxy)-2-benzothiazole sulfonamide

This product is synthesized in accordance with the procedure described in Example 2, except ethylsuccinyl chloride is substituted for ethyloxaloyl chloride.

EXAMPLE 4

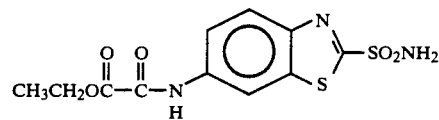

6-Ethyloxalylamino-2-benzothiazolesulfonamide

This product is synthesized in accordance with the procedure described in Example 2, except 6-aminobenzothiazolesulfonamide is substituted for 6-hydroxybenzothiozolesulfonamide.

EXAMPLE 5

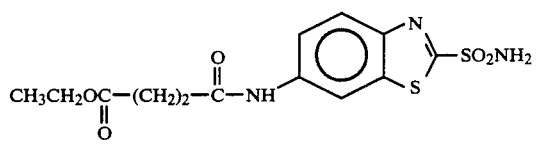

6-(Ethylsuccinylamino)-2-benzethiazolesulfonamide

This product is synthesized in accordance with the procedure described in Example 3 except 6-aminobenzothiazolesulfonamide is substituted for 6-hydroxybenzothiazolesulfonamide.

The cornea is lined on its posterior aspect by an endothelial cell layer. This endothelium serves to maintain corneal clarity, in part due to the action of carbonic anhydrase. Often (e.g., in conjunction with cataract surgery) it would be beneficial to have a functional test for corneal competence. These agents, when applied topically lead to a mild, transient swelling of the corneal which can readily be assessed by pachymtery. A competent cornea will return to normal thickness rapidly, while a compromised cornea (depressed endothelial function) will not recover as rapidly. This compromised patient is then a candidate for immediate corneal transplant, obviating the need for future inevitable surgery.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A compound of the formula

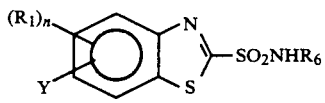

and pharmaceutically acceptable salts thereof wherein
$R_6$ is hydrogen or lower alkyl;
each $R_1$ is hydrogen, lower alkyl, halogen, nitro, trihaloalkyl, lower alkoxy, formyl, or lower alkanoyl, lower alkylamino or diloweralkylamino;

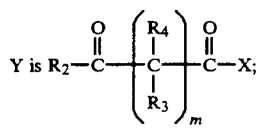

X is O, $NR_5$ or S;
$R_2$ is $OR_7$ or $NR_7 R_8$;
each $R_3$ and $R_4$ are independently hydrogen or lower alkyl;
$R_5$, $R_7$ and $R_8$ are independently hydrogen or lower alkyl;
n is 0-3 and
m is 0-6.

2. The compound according to claim 1 wherein $R_6$ is hydrogen.

3. The compound according to claim 1 wherein m is 0, 2, 4 or 6.

4. The compound according to claim 1 wherein one of $R_3$ and $R_4$ is hydrogen.

5. The compound according to claim 1 wherein $R_3$ and $R_4$ are both hydrogen.

6. The compound according to claim 1 wherein $R_1$ is

7. The compound according to claim 1 wherein $R_7$ is lower alkyl and $R_8$ is hydrogen.

8. The compound according to claim 1 wherein X is O or $NR_5$.

9. The compound according to claim 1 wherein X is $NR_5$.

10. The compound according to claim 1 having the formula

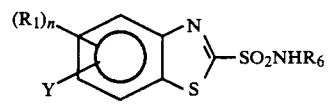

and pharmaceutically acceptable salts thereof wherein
$R_6$ is hydrogen or lower alkyl;
each $R_1$ is hydrogen, lower alkyl, halogen, nitro, trihaloalkyl, lower alkoxy, formyl, or lower alkanoyl, loweralkylamino, or diloweralkylamino;

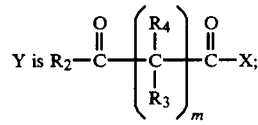

X is O, S or $NR_5$;
$R_2$ is $OR_7$, $NR_7 R_8$;
each $R_3$ and $R_4$ are independently hydrogen or lower alkyl;
$R_5$, $R_7$ and $R_8$ are independently hydrogen or lower alkyl;
n is 0-3 and
m is 0-6.

11. The compound according to claim 10 wherein $R_6$ is hydrogen.

12. The compound according to claim 10 wherein m is 0, 2, 4 or 6.

13. The compound according to claim 10 wherein one of $R_3$ and $R_4$ is hydrogen.

14. The compound according to claim 10 wherein $R_3$ and $R_4$ are hydrogen.

15. The compound according to claim 10 wherein $R_1$ is hydrogen.

16. The compound according to claim 10 wherein $R_7$ is lower alkyl and $R_8$ is hydrogen.

17. The compound according to claim 10 wherein X is O or $NR_5$.

18. The compound according to claim 17 wherein X is $NR_5$.

19. The compound according to claim 10 wherein Y is

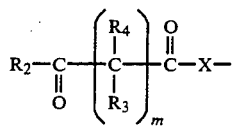

where $R_2$ is $OR_7$, $R_7$ is lower alkyl, each $R_3$ and $R_4$ are each independently hydrogen, n is 0, 2, 4 or 6 and X is $NR_5$.

20. The compound according to claim 10 wherein $R_6$ is lower alkyl.

21. The compound according to claim 10 wherein $R_6$ is methyl.

22. The compound according to claim 1 which is 6-(Ethyloxalyloxy)-2-benzothiazole sulfonamide 6-(Ethylsuccinyloxy)-2-benzothiazole sulfonamide, 6-ethyloxalylamino-2-benzothiazole sulfonamide or 6-ethylsuccinylamino-2-benzothiazole sulfonamide.

23. A pharmaceutical composition comprising a phramceutically effective amount of a compound according to claim 1 and a pharmaceutical carrier therefor.

24. A method of treating pathological diseases characterized by inappropriate carbonic anhydrase mediated secretion in mammals which comprises administering to said mammal an effective amount of a compound according to claim 1.

25. The method according to claim 24 wherein the disease is metabolic bone disease.

26. The method according to claim 24 wherein the metabolic bone disease is osteoporosis.

27. A method for treating glaucoma in a mammal which comprises administering to said mammal in need of such treatment an ocular hypotensive effective amount of the compound according to claim 1.

28. The method of claim 27 wherein the compound is dissolved or suspended in a carrier to be administered topically to the eye of the mammal.

29. The method of claim 27 wherein the compound is associated with a shield wafer or insert and is administered directly to the cornea of the mammal.

30. A method of assessment of corneal function in a mammal comprising administering to said mammal an effective amount of a compound according to claim 1.

31. The method of claim 30 wherein the compound is dissolved or suspended in a carrier to be administered topically to the eye of the mammal.

32. The method of claim 30 wherein the compound is associated with a shield wafer or insert and is administered directly to the cornea of the mammal.

* * * * *

UNITED STATES PATENT AND TRADEMARK OFFICE
CERTIFICATE OF CORRECTION

PATENT NO. : 5,059,613
DATED : October 22, 1991
INVENTOR(S) : William M. Pierce, Jr.

It is certified that error appears in the above-identified patent and that said Letters Patent is hereby corrected as shown below:

Column 1, lines 25-26: "in appropriate" should read as --inappropriate--

Column 7, line 11: "Y" should read as --Y is--

Col. 13, line 21, Claim 23: "phramceutically" should read as --pharmaceutically--

Column 14, line 17, Claim 30: "of" should read as --or--

Signed and Sealed this

Twenty-second Day of June, 1993

Attest:

MICHAEL K. KIRK

Attesting Officer

Acting Commissioner of Patents and Trademarks